(12) United States Patent
Sowa et al.

(10) Patent No.: US 7,407,745 B1
(45) Date of Patent: Aug. 5, 2008

(54) METHOD FOR SCREENING ANTICANCER AGENT

(75) Inventors: Yoshihiro Sowa, Kyoto (JP); Tetsuro Orita, Ibaraki (JP)

(73) Assignee: Chugai Seiyaku Kabushiki Kaisha, Tokyo (JP)

(*) Notice: Subject to any disclaimer, the term of this patent is extended or adjusted under 35 U.S.C. 154(b) by 0 days.

(21) Appl. No.: 09/937,162

(22) PCT Filed: Mar. 23, 2000

(86) PCT No.: PCT/JP00/01778

§ 371 (c)(1),
(2), (4) Date: Mar. 7, 2002

(87) PCT Pub. No.: WO00/56917

PCT Pub. Date: Sep. 28, 2000

(30) Foreign Application Priority Data

Mar. 23, 1999 (JP) ................................. 11/077350

(51) Int. Cl.
*C12Q 1/68* (2006.01)
(52) U.S. Cl. .......................................................... 435/6
(58) Field of Classification Search .................... 435/6, 435/320.1
See application file for complete search history.

(56) References Cited

FOREIGN PATENT DOCUMENTS

| JP | 60-149520 | 8/1985 |
| WO | WO 92/05286 | 4/1992 |

OTHER PUBLICATIONS

Sowa et al. (Cancer Research 1999. 59:4266-4270).*
Majello et al (J Biological Chemistry, 1997, 272:4021-4026, IDS).*
Kolell et al (Mol Biol Evl, 2002, 19:216-222).*
Bowie et al (Science, 1990, 257:1306-1310).*
Burgess et al (J of Cell Bio. 111:2129-2138, 1990).*
Scott et al (Nature Genetics, 1999, 21:440-443).*
Black et al (J of Cellular Physiology, 2001, 188:143-160).*
Gura (Science, 1997, 278:1041-1042).*
Jain (Sci. Am., 1994, 271:58-65).*
Curti (Crit. Rev. in Oncology/Hematology, 1993, 14:29-39).*
Dictionary-MSN Encarta, "potential", p. 1-3.*
Allen et al (TIBS, 1995, 20:511-516).*
Fields and Sternglanz (TIG, 1994, 10:287-292).*
Zips et al (2005, In Vivo, 19:1-7).*
Monneret, "Histone deacetylase inhibitors," Eur. J. Med. Chem. 40:1-13 (2005).
Kim et al., "Histone deacetylase in carcinogenesis and its inhibitors as anti-cancer agents," J. Biochem. Mol. Biol. 36(1):110-119 (2003).
Hasegawa et al., "Cloning of a GADD34-like Gene That Interacts with the Zinc-Finger Transcription Factor Which Binds to the p21[WAF] Promoter", *Biochemical and Biophysical Research Communications*. vol. 256(1). pp. 249-254 (1999).

Mo et al., "Down-Regulation of Topoisomerase IIa in CEM Cells Selected for Merbarone Resistance Is Associated with Reduced Expression of Sp3[1]", *Cancer Research*. vol. 57(22). pp. 5004-5008 (1997).
Dennig et al., "An inhibitor domain in Sp3 regulates its glutamine-rich activation domains", *The EMBO Journal*, vol. 15(20). pp. 5659-5667 (1996).
Majello et al., "Sp3 Is a Bifunctional Transcription Regulator with Modular Independent Activation and Repression Domains", *The Journal of Biological Chemistry*, vol. 272(7). pp. 4021-4026 (1997).
Lania et al., "Transcriptional Regulation by the Sp Family Proteins", *Int. J. Biochem. Cell. Biol.*, vol. 29(12), pp. 1313-1323 (1997).
Majello et al., "Different members of the Sp1 multigene family exert opposite transcriptional regulation of the long terminal repeat of HIV-1", *Nucleic Acids Research*. vol. 22(23), pp. 4914-4921 (1994).
Udvadia et al., "Functional interactions between the retinoblastoma (Rb) protein and Sp-family members: Superactivation by Rb requires amino acids necessary for growth suppression", *Proc. Natl. Aca. Sci. USA*. vol. 92(9), pp. 3953-3957 (1995).
Datto et al., "Functional Analysis of the Transforming Growth Factor β Responsive Elements in the WAF1/Cip1/p21 Promoter", J. Biol. Chem., 270:28623-28628, 1995.
Nakajima et al., "FR901228, a Potent Antitumor Antibiotic, Is a Novel Histone Deacetylase Inhibitor", Exp. Cell Res., 241:126-133, 1998.
Nakano et al., "Butyrate Activates the *WAF1/CipI* Gene Promoter through SP1 Sites in a p53-negative Human Colon Cancer Cell Line", J. Biol. Chem., 272:22199-22206, 1997.
Sowa et al., "Sp3, but not Sp1, Mediates the Transcriptionsl Activation of the p21/WAF1/Cip1 Gene Promoter by Histone Deacetylase Inhibitor", Cancer Res., 59:426604270, 1999.
Sowa et al., "Histone Deacetylase Inhibitor Activates the WAF1/Cip1 Gene Promoter through the Sp1 Sites", Biochem. Biophys. Res. Commun., 241:142-150, 1997.
Warrell, Jr., et al., "Therapeutic Targeting of Transcription in Acute Promyelocytic Leukemia by Use of an Inhibitor of Histone Deacetylase", J. Nat'l. Cancer Inst., 90:1621-1625, 1998.
Xiao et al., "Both Sp1 and Sp3 Are Responsible for p21[wafl] Promoter Activity Induced by Histone Deacetylase Inhibitor in NIH3T3 Cells", J. Cellular Biochem., 73:291-302, 1999.
Yoshida et al., "Potent and Specific Inhibition of Mammalian Histone Deacetylase Both in Vivo and in Vitro by Trichostatin A", J. Biol. Chem., 265:17174-17179, 1990.

* cited by examiner

*Primary Examiner*—Larry Helms
*Assistant Examiner*—Laura B Goddard
(74) *Attorney, Agent, or Firm*—Fish & Richardson P.C.

(57) ABSTRACT

By analyzing the mechanism for inducing a histone deacetylase inhibitor (Trichostatin A)-mediated expression of cyclin-CDK inhibitory factor having a proliferation suppressing effect (tumor-suppressing effect), it was revealed that the binding of Sp3 to the Sp1 binding sequence within a promoter is important in the expression of the above factor. Thus, a novel antitumor agent can be developed by screening a pharmaceutical agent capable of elevating Sp3 activity.

10 Claims, 4 Drawing Sheets

METHOD FOR SCREENING ANTICANCER AGENT

This application is the National Phase of International Patent Application No. PCT/JP00/01778, filed Mar. 23, 2000, and claims the benefit of Japanese patent application Ser. No. 11/77350, filed Mar. 23, 1999.

TECHNICAL FIELD

The present invention relates to a method for screening an anticancer agent. It specifically relates to a method for screening an anticancer agent targeting the Sp3 protein involved in the tumor-suppressing mechanism.

BACKGROUND ART

Cancer is caused by a series of genetic alterations destroying the normal mechanisms that control the cell cycle, differentiation, and morphology. A large number of natural compounds have been isolated based on their ability to restore cells having abnormal morphology, to induce cell differentiation, and to stop uncontrolled cell cycles in various cancer cells and transformed cells. Trichostatin A (TSA) (Sugita K et al. (1992). Cancer Res., 52, 168-172) and trapoxin (Itazaki H et al. (1990). J. Antibiot., 43, 1524-1532) have been isolated as substances capable of suppressing transformation. These substances also induce cell differentiation and cell cycle arrest. However, it was not clear how these materials showed such tumor-suppressing activity.

It is the current belief that histone deacetylases (HDAC) are the target of these drugs. Actually, TSA and trapoxin inhibit HDAC activity at the same concentration in which they show antitumor activity (Yoshida et al., 1990, J. Biol. Chem., 265: 17174-17179; Kijima M et al., 1993 J. Biol. Chem., 268, 22429-22435). Rapidly accumulating findings suggest that acetylation and deacetylation of histone and non-histone proteins play an important role in the transcriptional control of eukaryotic cells (Wolffe A P and Pruss D. (1996). Cell, 84, 817-819; Wade P A et al. (1997). TIBS, 22, 128-132; Pazin M J and Kadonaga J T. (1997). Cell, 89, 325-328; Struhl K. (1998). Genes Dev., 12, 599-606; Kuo M H and Allis C D. (1998). Bioessays, 20, 615-626). Since many transcription factors, transcription coactivators, and basic transcription initiation complex proteins have histone acetyltransferase activity, it became clear that acetylation of histone plays an important role in the initiation and promotion of transcription. Furthermore, the recent cloning of some of the HDACs, and the fact transcriptional repressors, and transcription corepressors form complexes with HDAC, gradually revealed that HDAC plays an important role in transcriptional repression (Wolffe A P. (1997). Nature, 387, 16-17). As HDAC inhibitors show antitumor activity, HDAC may repress transcription of a group of antitumor genes whose products induce cell proliferation arrest or cell differentiation (DePinho R A. (1998). Nature, 391, 533-536).

The present inventors earlier proved that sodium butyrate, which is well known as a differentiation inducer and acts as a HDAC inhibitor at micro molar concentrations, induced the expression of p21/WAF1/Cip1, which is a cyclin-CDK inhibitor (a negative regulator of cell cycle) acting independently of p53 (Nakano K et al. (1997). J. Biol. Chem., 272, 22199-22206). They also reported that both sodium butyrate and TSA activated p21/WAF1/Cip1 gene promoter through the Sp1 binding sequence (Sowa Y et al. (1997). Biochem. Biophys. Res. Comm., 241, 142-150). Interestingly, it was reported recently that the Sp1 binding site in p21/WAF1/Cip1 promoter was also involved in the induction of p21/WAF1/Cip1 by TGF-β, phorbol ester, okadaic acid, progesterone, or geranylgeranyl-transferase I inhibitor GGTI-298 (Datto M B et al. (1995). J. Biol. Chem., 270, 28623-28628; Biggs J R et al. (1996). J. Biol. Chem., 271, 901-906; Adnane J et al. (1998). Mol. Cell. Biol., 18, 6962-6970; Owen G I et al. (1998). J. Biol. Chem., 273, 10696-10701). Among these, TGF-β and GGTI-298 have been reported to induce transcription of p21/WAF1/Cip1 by enhancing the transcriptional activity of Sp1, whereas progesterone accomplishes the same through Sp1 and CBP/p300 (Li J M et al. (1998). Nucleic Acids Res., 26, 2449-2456; Owen G I et al. (1998). J. Biol. Chem., 273, 10696-10701).

These reports are thought to suggest the induction of transcription by SP1-mediated activation of histone acetyltransferase. Histone acetylation is thought to be involved in the transcriptional activation of many genes. In contrast, histone deacetylation is considered to be involved in transcriptional repression, although the detailed mechanism is not clear. Recently, it was reported that transcriptional repressors N-CoR and SMRT repressed the transcription specific to a DNA sequence by binding to intranuclear transcription factors (Horlein A J et al. (1995). Nature, 377, 397-404; Kurokawa R et al. (1995). Nature, 377, 451-454; Chen J D and Evans R M. (1995). Nature, 377, 454-457). As these factors bind to HDAC simultaneously and form a higher order complex, it is suggested that the rigid organization of chromatin, which is mediated by histone deacetylation, represses transcription (Pazin M J and Kadonaga J T. (1997). Cell, 89, 325-328; Heinzel T et al. (1997). Nature, 387, 43-48; Alland L et al. (1997) Nature, 387, 49-55). In fact, studies using a fusion protein of promyelocytic leukemia or promyelocytic leukemia zinc-finger protein and retinoic acid receptor revealed that the binding of HDAC was necessary for transcriptional repression (Lin R J et al. (1998). Nature, 391, 811-814; Grignani F et al. (1998). Nature, 391, 815-818; He L Z et al. (1998). Nature Genet., 18, 126-135). A similar HDAC-mediated mechanism of transcriptional repression specific to a DNA sequence was revealed also in the case of Myc/Mad/Max (Hassig C et al. (1997). Cell, 89, 341-347; Laherty C D et al. (1997). Cell, 89, 349-356), E2F/Rb (Brehm A et al. (1998). Nature, 391, 597-601; Magnaghi-Jaulin L et al. (1998). Nature, 391, 601-605; Luo R X et al. (1998). Cell, 92, 463-473), and in the case of DNA methylation (Nan X et al. (1998). Nature, 393, 386-389; Jones P L et al. (1998). Nature Genet., 19, 187-191). However, it was not clear whether or not a specific transcription factor capable of binding to the Sp1 binding sequence mediates the transcriptional activation signal by a HDAC inhibitor.

DISCLOSURE OF THE INVENTION

An objective of this invention is to provide an efficient method for screening an anticancer agent.

The present inventors reported that TSA, which is known to be a HDAC inhibitor having a tumor-suppressing effect, activated the p21/WAF1/Cip1 promoter through the Sp1 binding sequence (Nakano K et al. (1997). J. Biol. Chem., 272, 22199-22206; Sowa et al. (1997). Biochem, Biophys. Res. Comm., 241, 142-150). The inventors thought it might be possible to screen an anticancer agent targeting a novel molecule by identifying a new molecule involved in the signal transduction leading to the activation of the p21/WAF1/Cip1 promoter in response to a TSA stimulus.

Therefore, using gel mobility shift assays of the MG63 cell nuclear extract, the inventors first searched for factors that bound to the Sp1 binding sequence in the p21/WAF1/Cip1 promoter during the activation of the promoter by TSA. Thereby, they revealed that Sp1 and Sp3 were the main molecules that bound to the Sp1 binding sequence in the p21/WAF1/Cip1 promoter (Lania L et al. (1997). Int. J. Biochem. Cell Biol., 29, 1313-1323).

In addition to the p21/WAF1/Cip1 promoter, the inventors also examined the function of Sp1 and Sp3 by an assay system using the luciferase gene, which is activated depending on the GAL4 binding sequence, as the reporter gene. They revealed that transcriptional induction of the reporter gene by TSA occurred in the presence of GAL4-Sp3, which is a fusion protein of GAL4 and Sp3, but it did not occur in the presence of GAL4-Sp1, which is a fusion protein of GAL4 and Sp1. Furthermore, by constructing various Sp3 deletion mutants, they showed that transcriptional activation in response to a TSA stimulus could occur if at least one of the two glutamine-rich domains contained in the transcription activation domain was present. They also revealed that the forced expression of dominant negative Sp3 that lacks a transcription activation domain repressed the TSA-mediated activation of p21/WAF1/Cip1 promoter and that of the promoter activated through the Sp1 binding sequence.

These results prove that Sp3 is involved in the transcriptional activation of p21/WAF1/Cip1 by TSA. These results also suggest that the screening of anticancer agents targeting Sp3 might be possible. The assay system developed by the inventors using the luciferase gene activated depending on the GAL4 sequence as the reporter gene, is especially appropriate for efficiently screening anticancer agents.

This invention relates to a method for screening an anticancer agent targeting the Sp3 protein involved in tumor suppression. It especially relates to a method for efficiently screening an anticancer agent using the luciferase gene activated depending on the GAL4 binding sequence as the reporter gene. This invention specifically relates to:

(1) a method for screening an anticancer agent comprising the steps of:

(a) preparing a cell carrying (i) a first vector comprising, in an expressible manner, DNA encoding a fusion protein comprising a region having the transcriptional activation capacity of the Sp3 protein and a region having the DNA binding capacity of a heteroprotein, and, (ii) a second vector comprising a binding sequence of the heteroprotein, an expression regulatory sequence activated by the binding of the fusion protein, and a downstream reporter gene functionally bound to the regulatory sequence, (b) contacting a test sample with the cell and measuring reporter activity, and, (c) selecting a compound that elevates reporter activity in comparison with a control test in which the test sample is not contacted with the cell, (2) the method of (1), wherein the heteroprotein is the GAL4 protein, LexA protein, or tetracycline repressor protein, (3) the method of (1) or (2), wherein the reporter gene is encoding luciferase, chloramphenicol acetyltransferase, beta-galactosidase, human growth hormone, or secreted alkaline phosphatase, (4) an anticancer agent comprising a compound that enhances Sp3-mediated transcriptional activity as an active ingredient, and, (5) the anticancer agent of (4), wherein the agent can be isolated by a method of any one of (1) to (3).

As shown in the Examples, the transcription activation domain of Sp3 can elevate the transcription from p21/WAF1/Cip1 promoter. p21/WAF1/Cip1 gene has a cell proliferation suppressing effect, and its expression is elevated by TSA known to have a tumor-suppressing effect. The expression of p21/WAF1/Cip1 is also known to be induced through the Sp1 binding sequence by plural HDAC inhibitors closely related to antitumor effects. As this invention revealed that Sp3 was involved in the induction of transcription through the Sp1 binding sequence, it is thought that the treatment and prevention of cancer are also possible by enhancing the activity of Sp3 that suppresses cell neoplasia.

The method of this invention for screening an anticancer agent is based on the finding by the inventors that Sp3 is involved in the signal transduction leading to the expression of antitumor effects in response to a TSA stimulus. This method is also based on the finding that the system developed by the inventors for detecting the transcriptional activity of Sp3 using a reporter gene can also be used for the screening of a compound that has an antitumor effect similar to TSA.

The principle behind the screening method of this invention is as follows: First, the vectors are constructed. The first vector comprises, in an expressible manner, DNA encoding a fusion protein comprising a region having the transcriptional activation capacity of the Sp3 protein and a region having the DNA binding capacity of a heteroprotein. The second vector comprises the binding sequence of the heteroprotein, an expression regulatory sequence activated by the binding of the fusion protein, and a downstream reporter gene functionally bound to the regulatory sequence. These vectors are then introduced into a cell. In this cell, the fusion protein that comprises the region having transcriptional activation capacity of Sp3 protein and the region having DNA binding capacity of the heteroprotein is expressed through the first vector. The fusion protein binds to the expression regulatory region in the second vector through the DNA binding region derived from the heteroprotein. When a compound that acts positively upon an antitumor signal like TSA comes into contact with the cell, the expression of a reporter gene existing downstream of the expression regulatory region in the second vector is induced through the activation of transcription or cancellation of the transcriptional repression of the reporter gene through the transcription activation region derived from the Sp3 protein in the fusion protein. Therefore, if this assay system using the reporter gene is employed, an efficient, Sp3-mediated screening of an anticancer agent is possible by detecting the reporter activity in the cell after contacting the test sample and the cell.

Namely, the screening method of this invention includes the steps of (a) preparing a cell carrying (i) the first vector comprising, in an expressible manner, DNA encoding a fusion protein comprising a region having the transcriptional activation capacity of the Sp3 protein and a region having the DNA binding capacity of a heteroprotein and (ii) the second vector that comprises a binding sequence of the heteroprotein, an expression regulatory sequence activated by the binding of the fusion protein, and a downstream reporter gene functionally bound to the regulatory sequence, (b) bringing a test sample into contact with the cell and measuring the reporter activity, and (c) selecting a compound that elevates the reporter activity compared with a control test in which the test sample is not contacted with the cell.

The first vector used in the screening of this invention comprises, in an expressible manner, DNA encoding a fusion protein comprising a region having the transcriptional activation capacity of the Sp3 protein and a region having the DNA binding capacity of a heteroprotein. Comprising DNA in an expressible manner means that the DNA encoding the fusion protein is connected to the expression regulatory region (promoter or enhancer, for example) that ensures expression in the vector. For example, DNA encoding the fusion protein is inserted into the downstream of an appropriate promoter within the vector such as the CMV promoter, so that the vector can express the fusion protein in an appropriate host cell such as an animal cell or a yeast cell.

The region having transcriptional activation capacity of the Sp3 protein comprised in the fusion protein expressed by the first vector is not especially limited as long as it contains a region capable of transcriptional activation in response to a TSA stimulus. Desirably, such a region comprises at least a part of the transcription activation domain and lacks at least a part of the DNA binding domain. Although the screening of this invention is possible even in the presence of the DNA binding region derived from Sp3, the presence of this region is not desirable because a fusion protein comprising this region can bind to various endogenous Sp1 binding sequences. In the case of human Sp3 protein, a desirable region comprises at least one of the two glutamine-rich regions (amino acids 10-123 and 223-358) and lacks at least a part of the Zinc finger region (amino acids 495-517, 525-547, and 555-575) (Chris, K. et al., 1992, J. Biol. Chem., 12: 4251-4261). The species from which Sp3 protein derives is not limited. For example, Sp3 protein from humans, mammals, or other species can be used.

The region, specifically, amino acids 1-398, 81-398, 161-398, 1-320, 1-240, or 1-160 of human Sp3 protein as shown in FIG. 3 can be used appropriately for this invention, but it is not to be construed as being limited thereto.

The heteroprotein contained in the fusion protein expressed by the first vector is not specially limited as long as it can bind specifically to a specified DNA sequence. For example, the GAL4 protein, LexA protein (Gyuris, J. et al., 1993, Cell, 75: 791-803), tetracycline repressor protein (Tet R) (Manfred, G. et al., 1992, Proc. Natl. Acad. Sci. USA, 89: 5547-5551) can be used as a heteroprotein, but the heteroprotein is not to be construed as being limited thereto. Partial peptides of these proteins can also be used as long as they bind specifically to a specified DNA sequence. The region having DNA binding capacity of the heteroprotein can be, for example, peptides comprising the DNA binding domain of GAL4 protein (for example, amino acids 1-94 or 1-147), the DNA binding domain of LexA protein (for example, amino acids 1-202) (Erica, A. et al., 1992, Mol. Cell. Biol., 12: 3006-3014), and the DNA binding domain of tetracycline repressor protein (Tet R) (Manfred, G. et al., 1992, Proc. Natl. Acad. Sci. USA, 89: 5547-5551), but the peptides are not to be construed as being limited thereto.

The second vector of this invention comprises a binding sequence of the heteroprotein, the expression regulatory sequence activated by the binding of the fusion protein, and the downstream reporter gene functionally bound to the regulatory sequence.

The binding sequence of the heteroprotein used for the construction of the second vector of this invention is not specially limited as long as the fusion protein expressed by the first expression vector can bind specifically to the binding sequence. For example, if the fusion protein comprises the GAL4 DNA binding region, the binding sequence can be, for example, "5'-cggasgacwgtcstccg-3'; s=c or g, w=a or t" (Marmorstein, R. et al., 1992, Nature 356: 408-414). If the fusion protein comprises the LexA DNA binding region, the binding sequence can be, for example, "5'-ctgtnnnnnnnnnacag-3'; n=a, t, g, or c" (Erica, A. et al., 1992, Mol. Cell. Biol., 12: 3006-3014). If the fusion protein comprises the DNA binding domain of tetracycline repressor protein (Tet R), the binding sequence can be, for example, "5'-tccctatcagtgatagaga-3'" (Manfred, G. et al., 1992, Proc. Natl. Acad. Sci. USA, 89: 5547-5551).

It is desirable to use a binding sequence that is not recognized by endogenous proteins within the cell transfected by the vector. It is not desirable to use a sequence recognized by endogenous proteins because reporter activities generated in response to the actions of endogenous proteins may be detected.

To ensure that the downstream reporter gene is expressed when the fusion protein derived from the first vector binds to the binding sequence, a promoter sequence (such as the TATA sequence and Kozak sequence) can also be included in the second vector as an expression regulatory sequence in addition to the binding sequence.

When the DNA binding domain of GAL4 protein is used as the region having DNA binding capacity of the fusion protein derived from the first vector, the expression regulatory sequence used in the second vector can be, for example, the 5×GAL4 binding sequence, the E1B minimal promoter, and the DNA sequence containing TATA sequence.

In the second vector of the present invention, the reporter gene is functionally bound to the downstream of the expression regulatory sequence. The phrase "functionally bound" indicates that the reporter gene is bound to the expression regulatory sequence so as to be expressed in response to the binding of the fusion protein derived from the first vector to the expression regulatory sequence.

Although the reporter gene used for this invention is not specially limited as long as its product is detectable, it is desirable to use a gene whose product can be detected without complicated manipulations such as Northern blotting analysis or Western blotting analysis. Suitable reporter genes are, for example, the luciferase gene, chloramphenicol acetyltransferase (CAT) gene, beta-galactosidase (β-Gal) gene, human growth hormone (hGH) gene, and secreted alkaline phosphatase (SEAP) gene.

The cell used for the screening of this invention is not specially limited. For example, a human cell or a mammalian cell, such as MG63 cell (a cell line derived from human osteosarcoma) genetically lacking p53 can be used. A yeast cell or a cell of a microorganism such as *Escherichia coli* can also be used. A method known to one skilled in the art can be used for gene manipulations for constructing vectors, for the introduction of the vectors into the cell, etc.

In the screening of this invention, a test sample is brought to contact with the cell into which the two vectors described above have been introduced, and the reporter activity is measured.

The test sample used for the screening can be, for example, a purified protein (including antibodies), gene library, products of a gene library, synthetic peptide library, cell extract, cell culture supernatant, synthetic low molecular compound library, natural extract, but it is not to be construed as being limited thereto. The test sample can be contacted with the cell by a method such as adding the test sample to cell culture medium or introducing the test sample into the cell (including the introduction of the gene) according to the kind of test sample used.

Reporter activity can be detected by a method known to one skilled in the art according to the kind of reporter gene used. For example, when luciferase gene is used as the reporter gene, the substrate for luciferase is added to the cell extract, and the amount of the light emitted by the enzymatic reaction is detected by a luminometer. When CAT gene is used as the reporter gene, the amount of CAT in the cell extract can be detected by the ELISA method using anti-CAT antibodies. When beta-galactosidase gene is used, the substrate for beta-galactosidase is added to the cell extract, and the amount of the light emitted by the enzymatic reaction is detected by a luminometer. When human growth hormone (hGH) gene is used, the amount of hGH in cell culture can be detected by the ELISA method using anti-hGH antibodies. When secreted alkaline phosphatase (SEAP) gene is used as the reporter gene, the substrate for alkaline phosphatase is added to the cell culture, and the amount of light emitted by the enzymatic reaction can be detected by a luminometer.

If a significant increase in reporter activity is observed as a result of measuring reporter activity in comparison with a control test in which the test sample is not brought into contact with the cell, the test sample used becomes a candidate for a compound that inhibits proliferation of a tumor.

In this invention, it was shown that the transcriptional activity mediated by Sp3 was promoted in the signal transduction from TSA involved in the tumor-suppressing effect. This fact shows that a compound that can enhance the transcriptional activity mediated by Sp3 could have a tumor-suppressing effect. Thus, the present invention also relates to an anticancer agent comprising as an active ingredient a compound that enhances the transcriptional activity mediated by Sp3.

Such compounds that enhance Sp3 activity include various compounds having different sites of action. These compounds include, for example, those that act directly on Sp3 and promote its function, those that act upon molecules binding to Sp3 and promote function of Sp3 indirectly, those that act upon a group of proteins involved in the reaction from the binding of Sp3 to DNA to the transcription, those that inhibit the interaction between Sp3 and HDAC, those that inhibit the activity of HDAC, and those that inhibit the function of Sp1. These compounds can be isolated by the above-mentioned screening of this invention.

A compound of this invention which enhances the transcriptional activity mediated by Sp3 is thought to be applicable to a wide range of tumors. Because the induction of p21/WAF1/Cip1 expression mediated by Sp3 does not depend on p53, the compound is expected to be applicable especially to tumors having mutated or deleted p53.

When a compound of this invention that enhances the transcriptional activity mediated by Sp3 is used as a pharmaceutical agent, it can be formulated by well-known pharmaceutical manufacturing methods. For example, the compound can be administered as a formulation mixed properly with a pharmaceutically acceptable carrier or vehicle, specifically with sterile water, physiological saline, plant oil, emulsifier agent, suspending agent, detergent, stabilizer, etc.

The compound can be administered to patients by, for example, transdermal, intranasal, transbronchial, intramuscular, intravenous, or oral administration depending on the properties of the compound.

Although dosage can vary depending on age, weight, and symptoms of the patient, the method of administration, and so on, one skilled in the art can suitably select an appropriate dosage. If the compound can be encoded by DNA, gene therapy is also possible by integrating the DNA into a vector for gene therapy. Although the dosage and method of administration can vary depending on the weight, age, symptoms, and such of a patient, one skilled in the art can suitably select an appropriate dosage and a administration method.

BEST MODE FOR CARRYING OUT THE INVENTION

Figure 1:
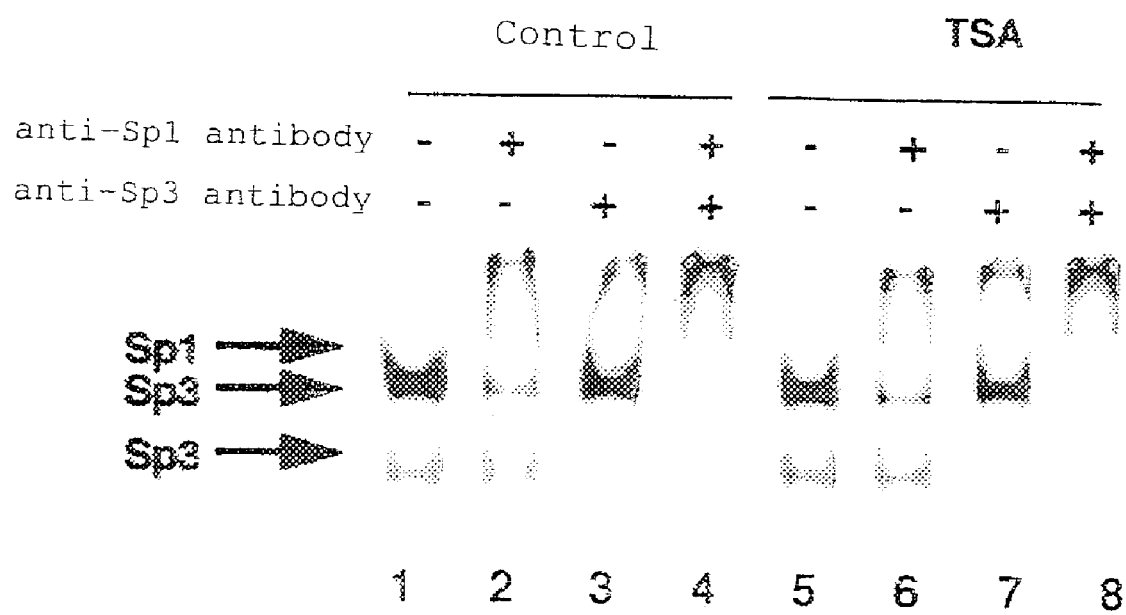
FIG. 1 is a photograph of a gel shift assay (EMSA) that shows the binding of Sp1 and Sp3 to the Sp1 binding sequence necessary for TSA dependent p21/WAF1/Cip1 promoter activation. EMSA was performed with nuclear extracts from both TSA-treated (lanes 5-9) and TSA-untreated (lanes 1-4) MG63 cells. The Sp1 binding sequence (positions −87 to −72 from the transcription start site), which is necessary for TSA dependent promoter activation, was used as a DNA probe. Supershift assay was carried out for each of the bands using anti-Sp1 antibodies (lanes 2, 4, 6, or 8) or anti-Sp3 antibodies (lanes 3, 4, 7, or 8). The positions of Sp1 and Sp3 bands are indicated on the left.

Hereinafter, this invention will be described in detail using specific examples, however it is not to be construed as being limited thereto.

Example 1 Gel Shift Assay of the Sp1 Binding Sequence in the p21/WAF1I/Cip1 Promoter TSA induces transcription of p21/WAF1/Cip1 gene in a p53-independent manner through the Sp1 binding sequence, which exists in the promoter region of the p21/WAF1/Cip1 gene. Therefore, to elucidate the induction mechanism, the −87 to −72 bp region from the transcription start site, which is essential for transcriptional induction by TSA was used as a p21/WAF1/Cip1 probe and the binding protein was analyzed by gel shift assay (electrophoretic mobility shift assay; EMSA) as described below.

(1-1) Cell Culture and Preparation of Nuclear Extracts

First, MG63 cells were incubated at 37° C. in a humidified atmosphere of 5% $CO_2$ using DMEM medium (GIBCO BRL) containing 10% fetal calf serum (GIBCO BRL). Nuclear extracts of these cells were prepared from both TSA-treated and untreated cells, according to the method of Dignam et al. (Dignam, J. D. et al., (1983) Nucleic Acids Res. 11:1475-1489). First, cells cultured in a dish (100 mm) were incubated for 24 hours with 500 ng/ml TSA (Wako). This was then washed twice with cold PBS containing 0.5 mM 4-(2-aminoethyl)benzenesulfonyl fluoride HCl (p-ABSF) (Wako), the cells were scraped from the plate, and suspended in 10 mM Hepes/KOH buffer (pH7.9) containing 10 mM KCl, 1.5 mM $MgCl_2$, 0.5 mM DTT, 5 mM NaF, 5 mM $NaVO_4$, and 0.5 mM p-ABSF. After placing on ice for 10 minutes, the cells were disrupted using a Dounce homogenizer. Upon centrifugation at 3,000 rpm for 10 minutes at 4° C., the nuclei were resuspended in 20 mM Hepes/KOH buffer (pH7.9) containing 400 mM NaCl, 1.5 mM $MgCl_2$, 25% glycerol, 0.1 mM EDTA, 1 mM DTT, 5 mM NaF, 5 mM $NaVO_4$, and 0.5 mM p-ABSF and mixed at 4° C. for 60 minutes to extract the nuclear components. This extract was centrifuged at 35,000 rpm for 30 minutes at 4° C. and the supernatant was recovered as nuclear extracts. The obtained nuclear extracts were dialyzed against 20 mM Hepes/KOH buffer (pH7.9) containing 400 mM KCl, 20% glycerol, 0.1 mM EDTA, 1 mM DTT, 5 mM NaF, 5 mM $NaVO_4$, and 0.5 mM p-ABSF, and were stored at −80° C.

(1-2) Gel Shift Assay (EMSA)

Next, based on the TSA-dependent promoter sequence (5'-CGGGTCCCGCCTCCTT-3'/SEQ ID NO: 1) located −87 to −72 bp from the transcription start site of the p21/WAF1/Cip1 gene, oligonucleotides (5'-AGCTCGGGTCCCGC-CTCCTT-3'/SEQ ID NO: 2, and 5'-TCGAAAGGAGGCGG-GACCCG-3'/SEQ ID NO: 3) were synthesized. Upon annealing, the DNAs were labeled using [$\alpha$-$^{33}$P] dCTP and Klenow Fragment (TAKARA), and these were used as DNA probes. After incubation of the abovementioned nuclear extract (8 μg) in 20 μl of reaction solution (8 mM Tris/HCl (pH7.9), 24 mM Hepes/KCl (pH7.9), 120 mM KCl, 24% glycerol, 2 mM EDTA, 2 mM DTT, 1 mg poly (dI-dC) (Pharmacia)) for 5 minutes, the $^{33}$P-labeled DNA probe (specific activity of 50,000 cpm/μl) was added and the binding reaction was allowed to proceed for 20 minutes. In the antibody supershift assay experiment, which will be described later, 2 μg of anti-Sp1 antibody or 1 μg of anti-Sp3 antibody (Santa Cruz, sc-59× and sc-644×) was further added and incubated for 20 minutes. The reaction solution was resolved by electrophoresis on a 6% acrylamide gel and the proteins that bind to the p21/WAF1/Cip1 probe were detected using BAS 2000 (Fujix).

(1-3) Result

When the nuclear extract prepared from TSA-treated and untreated MG63 cells were reacted with the p21/WAF1/Cip1 probe, and the gel shift assay described above was carried out, two specific bands were detected (FIGS. 1, 1 and 5). Next, when the reactivity of each of the supershifted bands was observed by the abovementioned method using anti-Sp1 or anti-Sp3 antibody, a portion of the upper band shifted in the presence of the anti-Sp1 antibody, two bands including a portion of the upper band and the lower band shifted in the presence of anti-Sp3 antibody, and all bands shifted when both anti-Sp1 antibody and anti-Sp3 antibody were added (FIG. 1). The two Sp3 bands are thought to originate from large (97 kDa) and small (60 kDa and 65 kDa) Sp3 proteins, respectively (Gustav, H. et al., (1994) EMBO J. 13: 3843-3851; Addanki, P. B. et al., (1997) Nucleic Acids Res. 25: 2012-2019). Therefore, Sp1 and Sp3 present in the nuclear extract of MG63 cells were actually shown to bind to the Sp1 binding region of p21/WAF1/Cip1, and this suggested that Sp1 and Sp3 were involved in TSA dependent transcriptional induction. These results are consistent with previous reports made by the inventors (Nakano, K. et al., (1997) J. Biol. Chem. 272: 22199-22206) and by other groups (Datto, M. B. et al., (1995) J. Biol. Chem. 270: 28623-28628; Adnane, J. et al., (1998) Mol. Cell. Biol. 18: 6962-6970). However, a difference in the amount of DNA bound by Sp1 and Sp3 due to the presence or absence of TSA treatment could not be observed (FIG. 1). Therefore, TSA dependent transcriptional induction seemed to take place through mechanisms other than differences in the amount of Sp1 or Sp3 expressed, or differences in their ability to bind to DNA. This is also consistent with the inventors' report using sodium butyrate, an HDAC inhibitor (Nakano, K. et al., (1997) J. Biol. Chem. 272: 22199-22206) and with the report by Datto et al. observing TGF-β-dependent transcriptional induction (Datto, M. B. et al., (1995) J. Biol. Chem. 270: 28623-28628), but is inconsistent with the report by Adnane et al. using geranyl geranyl-transferase I inhibitor (Adnane, J. et al., (1998) Mol. Cell. Biol. 18: 6962-6970).

Example 2 Reporter Assay Using the GAL4 Binding Sequence

TSA causes transcriptional induction through the Sp1 binding sequence of the p21/WAF1/Cip1 promoter, and similarly, it can cause transcriptional induction through the 3×Sp1 consensus binding sequence inserted into the SV40 promoter (Sowa, Y. et al., (1997) Biochem. Biophys. Res. Comm. 241: 142-150). Consequently, to determine whether Sp1 or Sp3 that bind to this Sp1 binding sequence is actually involved in transcriptional induction caused by TSA treatment, a reporter assay system using the GAL4 binding sequence was examined. Namely, when trying to observe effects of Sp1 or Sp3 by forced expression, endogenous effects of Sp1 or Sp3 will be detected if the Sp1 binding sequence is used as a promoter for the reporter gene. Therefore, forced expression of a fusion protein formed between the DNA binding domain of bacterial GAL4 protein and Sp1 or Sp3 allowed analysis of whether GAL4 binding sequence-dependent transcriptional activity is induced by TSA or whether Sp1 or Sp3 regulates this induction.

(2-1) Expression Plasmid and Reporter Plasmid

To express GAL4 proteins that have Sp1 (amino acids 83-778), full-length Sp3 (amino acids 1-653), transcriptional activation domain-deleted Sp1 (amino acids 592-778) (DNSp1), or transcriptional activation domain-deleted Sp3 (amino acids 399-653) (DNSp3) attached to the C-terminal end of their DNA binding domain, each of these genes were inserted into a pM vector (Clontech) possessing a GAL4 binding domain. This yielded pM-Sp1, pM-Sp3, pM-DNSp1, and pM-DNSp3, respectively. Each of the Sp1 and Sp3 genes was amplified by PCR. Specifically, pM-Sp1 production employed Sp1-S (5'-acaggtgagcttga-3'/SEQ ID NO: 4) and Sp1-AS (5'-tcagaagccattgcc-3'/SEQ ID NO: 5) as primers and used pPacSp1 as template for amplification (Kadonaga, J. T. et al., (1987) Cell 51:1079-1090). pM-DNSp1 production employed DNSp1-S (5'-ccaaaaaagaagagaaaggtaacccggcgg-3'/SEQ ID NO: 6) and DNSp1-AS (5'-gaagcatgcacctgc-3'/SEQ ID NO: 7) as primers and used pM-Sp1 as template for amplification (Kadonaga, J. T. et al., (1987) Cell 51: 1079-1090). pM-Sp3 production employed Sp3-18F (5'-cgggatc-cattccaagtgctgct-3'/SEQ ID NO: 8) and Sp3-2R (5'-ataggatc-cttactccattgtctcatttcc-3'/SEQ ID NO: 9) as primers and used Marathon-Ready cDNA (Human Fetal Liver) (Clontech, Cat. #7403-1) as template for amplification (Chris, K. et al., (1992) J. Biol. Chem. 12: 4251-4261). pM-DNSp3 production employed Sp3-11F (5'-cgggatccaactctatagattctgct-3'/SEQ ID NO: 10) and Sp3-2R (SEQ ID NO: 9) as primers and used pM-Sp3 as template for amplification (Chris, K. et al., (1992) J. Biol. Chem. 12: 4251-4261). All PCRs were carried out by performing 30 cycles of 94° C. for 1 minute, 55° C. for 30 seconds, and 72° C. for 30 seconds. The resulting PCR amplified product was inserted into a pM vector and the nucleotide sequence was confirmed using a DNA sequencer, ABI PRISM 355 (Applied Bio System). As a control for the transfection test, pM that only expresses the GAL4 DNA binding domain was employed. The reporter plasmid (pG5-luc) used to indicate the dependence of transcriptional activation, on GAL4 was pGL3-Basic Vector (Promega), which carried the 5×GAL4 binding sequence, E1B minimum promoter, and TATA sequence, upstream of the luciferase gene.

(2-2) Transfection Assay

The expression vector described above encoding various Sp1 or Sp3 GAL4 fusion proteins and the abovementioned vector carrying a luciferase reporter gene downstream of the consensus 5×GAL4 binding sequence were cotransfected into MG63 cells using SuperFect following the method by QIAGEN. Namely, cells were seeded at a density of 0.8×105 cells/well in a 12-well plate. After 24 hours, a pre-mixed reaction solution containing 0.5 μg of reporter plasmid, 2.5 μg of expression vector, and SuperFect were added to the MG63 cells and the mixture was reacted for 2 hours. Subsequently, the cells were cultured for 24 hours under normal culture conditions, cultured for another 24 hours with or without (control) 500 ng/ml of TSA, and then, the cells were lysed. Using luciferase substrate (Promega), luciferase activity of the cell lysates was measured using LB-96P (Berthold). The measured values were normalized and were expressed as activity per amount of protein. Transcriptional induction due to TSA treatment was calculated as a ratio with respect to the TSA-untreated control value (activation amplification by TSA).

(2-3) Result

Figure 2:
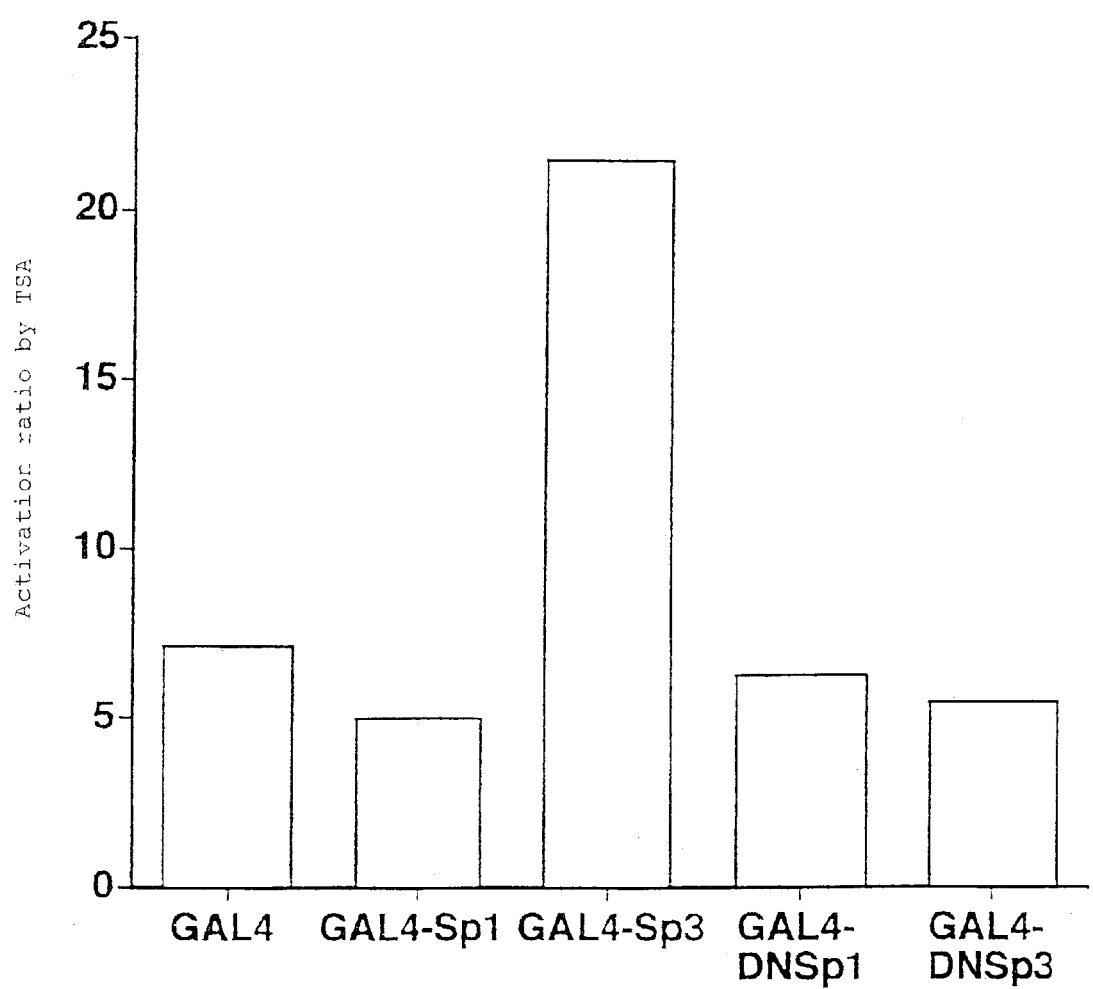
FIG. 2 shows TSA dependent transcriptional induction by Sp3. MG63 cells were cotransfected with 2.5 μg of either GAL4-Sp1 or GAL4-Sp3 plasmid and with 0.5 μg of pG5-luc reporter plasmid. At 24 hours posttransfection, TSA (500 ng/ml) was added, 24 hours later, the cells were lysed, and luciferase activity was measured. Transcriptional induction by TSA is expressed as a ratio with respect to the TSA-untreated control value. Each experiment was carried out in triplicates and the data shown is a representative of five independent experiments.

Although GAL4-Sp1 and GAL4-Sp3 both showed transcriptional activity even without TSA treatment, this seemed to be mediated through the transcriptional activation domain present within Sp1 and Sp3 themselves. When treated with TSA, cells expressing GAL4-Sp3 showed strong transcriptional induction of the luciferase gene, whereas activity in the cells expressing GAL4-Sp1 was similar in magnitude to that seen in the control using GAL4 (FIG. 2). Furthermore, when a similar study was carried out with the fusion protein made from the N-terminal end transcriptional activation domain-deleted Sp1 or Sp3, and the GAL4 DNA binding domain, described above, GAL4-DNSp3 no longer showed TSA dependent transcriptional induction (FIG. 2). These results suggested that transcriptional induction of the p21/WAF1/Cip1 gene by TSA treatment occurs through the transcriptional activation domain of Sp3, bound to the Sp1 binding sequence of the promoter.

Example 3 Identification of the TSA Responsive Domain of Sp3

Next, reporter assay was performed using various Sp3 deletion mutants fused to the GAL4 DNA binding domain in order to identify the TSA responsive region of Sp3. First, pM-Sp3 (1-398), pM-Sp3 (81-398), pM-Sp3 (161-398), pM-Sp3 (241-398), pM-Sp3 (1-80), pM-Sp3 (1-160), pM-Sp3 (1-240), and pM-Sp3 (1-320) were prepared. They respectively carry regions corresponding to the indicated amino acid numbers. Each of the Sp1 and Sp3 genes were amplified by PCR, inserted into a pM vector, and the nucleotide sequences were confirmed using a DNA sequencer, ABI PRISM 355 (Applied Bio System). The primer sequences used for PCR amplification are shown in Table 1. PCR was carried out using pM-Sp3 as the template, performing 25 cycles of 98° C. for 15 seconds, 65° C. for 2 seconds and 74° C. for 30 seconds.

TABLE 1

| Plasmid | Primer |
| --- | --- |
| pM-Sp3(1-398) | Sp3-18F<br>(5'-cgggatccattccaagtgctgct-3'/SEQ ID NO: 8)<br>Sp3(1194-1177)AS + BamHI<br>(5'-gcggatcccactgtaactgtttgtag-3'/SEQ ID NO: 11) |
| pM-Sp3(81-398) | Sp3(241-260) S + BamHI<br>(5'-cgggatccggctctaatcaaaccttact-3'/SEQ ID NO: 12)<br>Sp3(1194-1177)AS + BamHI (SEQ ID NO: 11) |
| pM-Sp3(161-398) | Sp3(481-500) S + BamHI<br>(5'-cgggatccggcattaatgccgacggaca-3'/SEQ ID NO: 13)<br>Sp3(1194-1177)AS + BamHI (SEQ ID NO: 11) |
| pM-Sp3(241-398) | Sp3(721-740) S + BamHI;<br>(5'-cgggatcccagggaaattatatccagtc-3'/SEQ ID NO: 14)<br>Sp3(1194-1177)AS + BamHI (SEQ ID NO: 11) |
| pM-Sp3(1-80) | Sp3-18F (SEQ ID NO: 8)<br>Sp3(240-221)AS + BamHI<br>(5'-cgggatccaggaatgatctgaatttgac-3'/SEQ ID NO: 15) |
| pM-Sp3(1-160) | Sp3-18F (SEQ ID NO: 8)<br>Sp3(480-461)AS + BamHI<br>(5'-cgggatcctgcagtcattgtctgagaac-3'/SEQ ID NO: 16) |
| pM-Sp3(1-240) | Sp3-18F (SEQ ID NO: 8)<br>Sp3(720-701)AS + BamHI<br>(5'-cgggatccaagatctgaagaatgaacct-3'/SEQ ID NO: 17) |
| pM-Sp3(1-320) | Sp3-18F (SEQ ID NO: 8)<br>Sp3(960-941)AS + BamHI<br>(5'-cgggatccaaaggttccaggattcagct-3'/SEQ ID NO: 18) |

Figure 3:
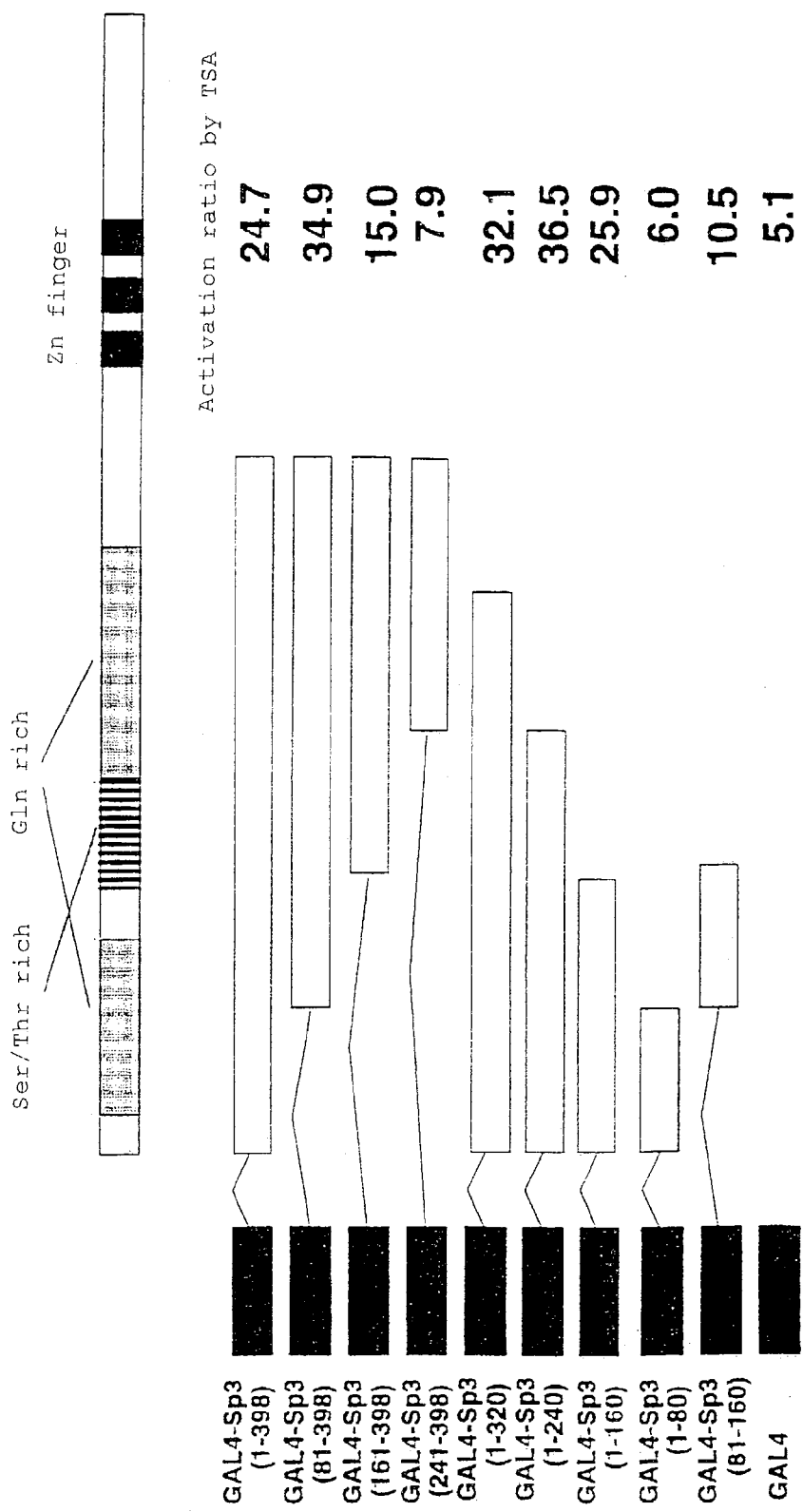
FIG. 3 shows TSA dependent transcriptional induction mediated by the Sp3 glutamine-rich domain. Sequences of various GAL4-Sp3 deletion mutant proteins are indicated in the figure. The magnitudes of transcriptional induction by TSA upon expressing each of these proteins in the MG63 cells are indicated on the right. Transfection and TSA treatment were performed similarly to FIG. 2. Each experiment was carried out in triplicates and the data shown is a representative of three independent experiments.

As a control for the transfection test, pM expressing only the GAL4 DNA binding domain was used. The reporter plasmid (pG5-luc) used as an index for GAL4 dependent transcriptional activation was the abovementioned pGL3-Basic Vector (Promega). Transfection using these genes followed the same method as described above, and the occurrence of transcriptional induction due to TSA treatment in these mutants was monitored. Consequently, TSA dependent transcriptional induction occurred with GAL4-Sp3 (1-398) that lacks the Sp3 DNA binding domain (FIG. 3), and this induction was in fact stronger than with GAL4-Sp3 (FIG. 3). This result correlated with the aforementioned result (Example 2) where deletion of the N-terminal end transcriptional activation domain caused the termination of transcriptional induction due to TSA treatment. This also suggested a correlation with the report describing that of the two glutamine-rich domains in Sp3, the repressive domain existing between the C-terminal domain and the DNA binding domain represses the transcriptional activation of Sp3 (Dennig, J. et al., (1996) EMBO J. 15: 5659-5667; Majello B et al., (1997) J. Biol. Chem. 272: 4021-4026).

As FIG. 3 shows, when deletions were made from the N-terminal end or from the C-terminal end of Sp3 (1-398), induction due to TSA treatment disappeared with GAL4-Sp3 (241-398) and with GAL4-Sp3 (1-80). From these results, Sp3 (81-160) seemed important for transcriptional induction due to TSA treatment. However, GAL4-Sp3 (81-160) alone showed almost no activity. Since both GAL4-Sp3 (241-398) and GAL4-Sp3 (1-80) lack a complete glutamine-rich domain, transcriptional induction by TSA seems to require the presence of at least one of the two glutamine-rich domains in the Sp3 transcriptional activation domain. The 80-160 region of Sp3 may contain part of an important region for TSA mediated transcriptional induction.

Example 4 Dominant Negative Sp3

Moreover, to determine whether Sp3 actually mediates transcriptional induction by TSA through the Sp1 binding sequence of p21/WAF1/Cip1, the transcriptional activation domain was deleted, and a Sp3 mutant (DNSp3) (amino acid 399-653) which only has the DNA binding domain was integrated into pCMV3.1-His-C (Invitrogen) to produce pCMV-DNSp3. pCMV3.1 was used as a control. The reporter plasmids used were pWWP and pWPdel-BstXI, which have the previously reported p21/WAF1/Cip1 promoter and the TSA dependent p21/WAF1/Cip1 minimum promoter inserted upstream of the luciferase gene, respectively, and Sp1-luc and mtSp1-luc, which have 3×Sp1 binding sequence and mutant 3×Sp1 binding sequence inserted upstream of the luciferase gene, respectively (Nakano, K. et al., (1997) J. Biol. Chem. 272: 22199-22206; Sowa, Y. et al., (1997) Biochem. Biophys. Res. Comm. 241: 142-150).

Figure 4:
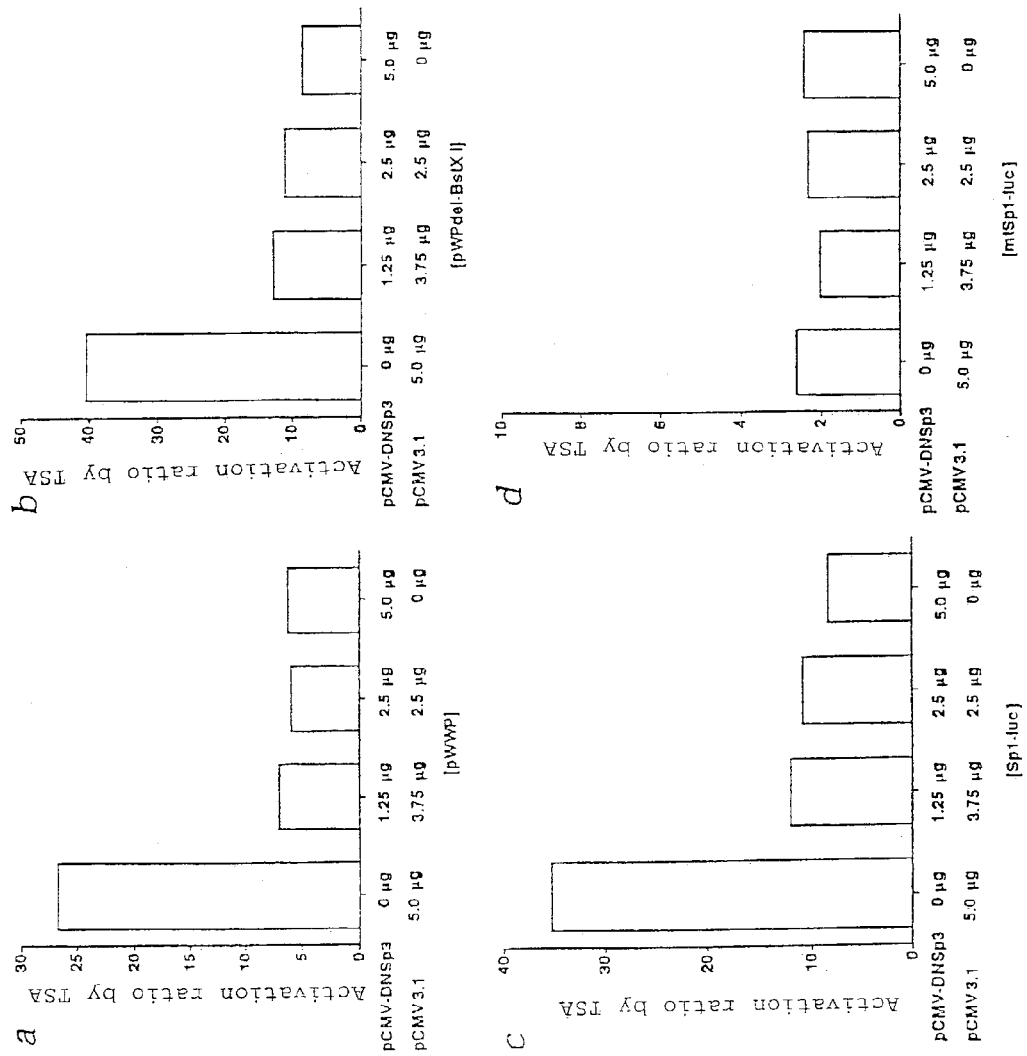
FIG. 4 shows the repression of TSA dependent transcriptional induction of either the p21/WAF1/Cip1 promoter or the Sp1 promoter by dominant negative Sp3. MG63 cells were simultaneously transfected with 0, 1.25, 2.5, or 5.0 μg of pCMV-DNSp3 while adjusting the total amount of plasmids to 5.0 μg by adding pCMV3.1 control plasmid, and with 0.5 μg of reporter plasmid, pWWP (a), pWPdel-BstXI (b), Sp1-luc (c), or mtSp1-luc (d). Transfection and TSA treatment was performed similarly to FIG. 2. Each experiment was carried out in triplicates and the data shown is a representative of three independent experiments.

Through forced expression of these genes by transfection using the same method as described above, the inventors examined whether these genes function in a dominant negative fashion towards transcriptional induction by TSA. Consequently, transcriptional induction of p21/WAF1/Cip1 by TSA was remarkably repressed by DNSp3 and this was confirmed by pWPdel-BstXI as well, which has the smallest unit of TSA dependent p21/WAF1/Cip1 promoter that carries the Sp1 binding sequence (+16 to −101 from the transcription start site) (FIG. 4a, b). Similarly, TSA dependent transcriptional induction driven by the consensus Sp1 binding sequence showed marked repression (FIG. 4c). When the mutated Sp1 binding sequence was used, transcriptional induction by TSA did not take place, and the effect of DNSp3 was absent as well (FIG. 4d). In either promoter, DNSp3 did not show repression towards TSA-untreated basic transcriptional activity. These results revealed the importance of the Sp3 transcriptional activation domain in TSA dependent p21/WAF1/Cip1 transcriptional induction. It is assumed that in the absence of TSA treatment, Sp3 only has extremely weak transcriptional factor activity, however, in the presence of TSA treatment, a molecule acetylated by repression of HDAC is recognized and subsequently strong transcriptional activity is expressed.

Recently, as a new approach against cancer, transcription-regulating chemotherapy and transcription-regulating chemoprevention were proposed (Sakai, T., (1996) Jpn. J. Hyg. 50: 1036-1046). The strategy is to induce the transcription of cell-proliferation suppressive p53 target genes, thereby exhibiting anticancer activity. However, as a target for transcriptional induction, the finding that p53 is mutated in many human tumor cells (Sakai, T., (1996) Jpn. J. Hyg. 50: 1036-1046; Vogelstein, B. and Kinzler, K. W., (1992) Cell 70: 523-526) is a drawback. In contrast, almost no mutation has been reported in human cancer cells for p21/WAF1/Cip1, which is one of the target genes of p53 and has cell-cycle suppressing activity (Chedid, M et al., (1994) Oncogene 9: 3021-3024; Li, Y. J. et al., (1995) Oncogene 10: 599-601). Therefore, anticancer activity can be expected through transcriptional induction of p21/WAF1/Cip1. This invention revealed that a pathway exists for p53 independent p21/WAF1/Cip1 transcriptional induction mediated by histone acetylation, and suggests that transcription-regulating chemotherapy or transcription-regulating chemoprevention of cancer is possible even when p53 is mutated. HDAC inhibitors are regarded as possible drugs, and in reality, sodium phenylbutyrate, an HDAC inhibitor previously used for the treatment of thalassemia and hyperammonemic states, in combination with all-trans retinoic acid was shown to induce complete remission of all-trans-retinoic acid resistant acute promyelocytic leukemia (Warrel, R. P., Jr. et al., (1998) J. Natl. Cancer Inst. 90: 1621-1625). These results suggest HDAC as one of the possible target molecules for cancer therapy.

INDUSTRIAL APPLICABILITY

This invention showed that Sp3, which regulates HDAC, could be a new target molecule for cancer therapy. This invention also provided an efficient Sp3-targeted method for screening antitumor agents. Compounds isolated by the screening method of this invention are expected to be applied in novel transcription-regulating chemotherapy and chemoprevention against cancer.

The invention claimed is:

1. A method of identifying an agent that activates TSA-responsive Sp3-mediated transcription, the method comprising:
providing a mammalian cell in vitro having
(a) a first vector comprising a first regulatory sequence operably linked to a nucleic acid sequence encoding a fusion protein, wherein the fusion protein comprises:
(i) a fragment of human Sp3 (1) having transcriptional activation activity, and (2) comprising at least one glutamine rich region of a TSA responsive domain of human Sp3, wherein at least amino acids 495-517, 525-547, and 555-575 of the Sp3 Zinc finger region are lacking from said fragment of human Sp3, and
(ii) a DNA binding domain of a heterologous protein; and
(b) a second vector comprising a target binding sequence for the DNA binding domain of the fusion protein operably linked to a reporter gene;
contacting the cell with a test agent; and
selecting a test agent that increases the expression of the reporter gene compared to a control.

2. The method of claim 1, wherein the heterologous protein is not endogenous to the cell.

3. The method of claim 2, wherein the heterologous protein is GAL4, LexA or tetracycline repressor.

4. The method of claim 1, wherein the reporter gene encodes luciferase, chloramphenicol acetyltransferase, beta-galactosidase, human growth hormone or secreted alkaline phosphatase.

5. The method of claim 3, wherein the reporter gene encodes luciferase, chloramphenicol acetyltransferase, beta-galactosidase, human growth hormone or secreted alkaline phosphatase.

6. The method of claim 1, wherein the second vector comprises a second regulatory sequence operably linked to the reporter gene.

7. The method of claim 3, wherein the second vector comprises a second regulatory sequence operably linked to the reporter gene.

8. The method of claim 4, wherein the second vector comprises a second regulatory sequence operably linked to the reporter gene.

9. The method of claim 1, wherein the test agent is a low molecular weight compound.

10. The method of claim 1, wherein the fusion protein comprises at least one of the two glutamine-rich regions comprising amino acids 10-123 or 223-358 of human Sp3.

* * * * *

SEQUENCE LISTING

<160> NUMBER OF SEQ ID NOS: 21

<210> SEQ ID NO 1
<211> LENGTH: 16
<212> TYPE: DNA
<213> ORGANISM: Artificial Sequence
<220> FEATURE:
<223> OTHER INFORMATION: an artificially synthesized oligonucleotide
      sequence

<400> SEQUENCE: 1
cgggtcccgc ctcctt                                                       16

<210> SEQ ID NO 2
<211> LENGTH: 20
<212> TYPE: DNA
<213> ORGANISM: Artificial Sequence
<220> FEATURE:
<223> OTHER INFORMATION: an artificially synthesized oligonucleotide
      sequence

<400> SEQUENCE: 2
agctcgggtc ccgcctcctt                                                   20

```
<210> SEQ ID NO 3
<211> LENGTH: 20
<212> TYPE: DNA
<213> ORGANISM: Artificial Sequence
<220> FEATURE:
<223> OTHER INFORMATION: an artificially synthesized oligonucleotide
      sequence

<400> SEQUENCE: 3
tcgaaaggag gcgggacccg                                                   20

<210> SEQ ID NO 4
<211> LENGTH: 14
<212> TYPE: DNA
<213> ORGANISM: Artificial Sequence
<220> FEATURE:
<223> OTHER INFORMATION: primer

<400> SEQUENCE: 4
acaggtgagc ttga                                                         14

<210> SEQ ID NO 5
<211> LENGTH: 15
<212> TYPE: DNA
<213> ORGANISM: Artificial Sequence
<220> FEATURE:
<223> OTHER INFORMATION: primer

<400> SEQUENCE: 5
tcagaagcca ttgcc                                                        15

<210> SEQ ID NO 6
<211> LENGTH: 30
<212> TYPE: DNA
<213> ORGANISM: Artificial Sequence
<220> FEATURE:
<223> OTHER INFORMATION: primer

<400> SEQUENCE: 6
ccaaaaaaga agagaaaggt aacccggcgg                                        30

<210> SEQ ID NO 7
<211> LENGTH: 15
<212> TYPE: DNA
<213> ORGANISM: Artificial Sequence
<220> FEATURE:
<223> OTHER INFORMATION: primer

<400> SEQUENCE: 7
gaagcatgca cctgc                                                        15

<210> SEQ ID NO 8
<211> LENGTH: 23
<212> TYPE: DNA
<213> ORGANISM: Artificial Sequence
<220> FEATURE:
<223> OTHER INFORMATION: primer

<400> SEQUENCE: 8
cgggatccat tccaagtgct gct                                               23

<210> SEQ ID NO 9
<211> LENGTH: 30
<212> TYPE: DNA
<213> ORGANISM: Artificial Sequence
```

```
<220> FEATURE:
<223> OTHER INFORMATION: primer

<400> SEQUENCE: 9
ataggatcct tactccattg tctcatttcc                                          30

<210> SEQ ID NO 10
<211> LENGTH: 26
<212> TYPE: DNA
<213> ORGANISM: Artificial Sequence
<220> FEATURE:
<223> OTHER INFORMATION: primer

<400> SEQUENCE: 10
cgggatccaa ctctatagat tctgct                                              26

<210> SEQ ID NO 11
<211> LENGTH: 26
<212> TYPE: DNA
<213> ORGANISM: Artificial Sequence
<220> FEATURE:
<223> OTHER INFORMATION: primer

<400> SEQUENCE: 11
gcggatccca ctgtaactgt ttgtag                                              26

<210> SEQ ID NO 12
<211> LENGTH: 28
<212> TYPE: DNA
<213> ORGANISM: Artificial Sequence
<220> FEATURE:
<223> OTHER INFORMATION: primer

<400> SEQUENCE: 12
cgggatccgg ctctaatcaa accttact                                            28

<210> SEQ ID NO 13
<211> LENGTH: 28
<212> TYPE: DNA
<213> ORGANISM: Artificial Sequence
<220> FEATURE:
<223> OTHER INFORMATION: primer

<400> SEQUENCE: 13
cgggatccgg cattaatgcc gacggaca                                            28

<210> SEQ ID NO 14
<211> LENGTH: 28
<212> TYPE: DNA
<213> ORGANISM: Artificial Sequence
<220> FEATURE:
<223> OTHER INFORMATION: primer

<400> SEQUENCE: 14
cgggatccca gggaaattat atccagtc                                            28

<210> SEQ ID NO 15
<211> LENGTH: 28
<212> TYPE: DNA
<213> ORGANISM: Artificial Sequence
<220> FEATURE:
<223> OTHER INFORMATION: primer

<400> SEQUENCE: 15
cgggatccag gaatgatctg aatttgac                                            28
```

```
<210> SEQ ID NO 16
<211> LENGTH: 28
<212> TYPE: DNA
<213> ORGANISM: Artificial Sequence
<220> FEATURE:
<223> OTHER INFORMATION: primer

<400> SEQUENCE: 16
cgggatcctg cagtcattgt ctgagaac                                              28

<210> SEQ ID NO 17
<211> LENGTH: 28
<212> TYPE: DNA
<213> ORGANISM: Artificial Sequence
<220> FEATURE:
<223> OTHER INFORMATION: primer

<400> SEQUENCE: 17
cgggatccaa gatctgaaga atgaacct                                              28

<210> SEQ ID NO 18
<211> LENGTH: 28
<212> TYPE: DNA
<213> ORGANISM: Artificial Sequence
<220> FEATURE:
<223> OTHER INFORMATION: primer

<400> SEQUENCE: 18
cgggatccaa aggttccagg attcagct                                              28

<210> SEQ ID NO 19
<211> LENGTH: 17
<212> TYPE: DNA
<213> ORGANISM: Artificial Sequence
<220> FEATURE:
<223> OTHER INFORMATION: exemplary motif

<400> SEQUENCE: 19
cggasgacwg tcstccg                                                          17

<210> SEQ ID NO 20
<211> LENGTH: 16
<212> TYPE: DNA
<213> ORGANISM: Artificial Sequence
<220> FEATURE:
<223> OTHER INFORMATION: exemplary motif
<220> FEATURE:
<221> NAME/KEY: misc_feature
<222> LOCATION: (1)...(16)
<223> OTHER INFORMATION: n = A,T,C or G

<400> SEQUENCE: 20
ctgtnnnnnn nnacag                                                           16

<210> SEQ ID NO 21
<211> LENGTH: 19
<212> TYPE: DNA
<213> ORGANISM: Artificial Sequence
<220> FEATURE:
<223> OTHER INFORMATION: exemplary motif

<400> SEQUENCE: 21
tccctatcag tgatagaga                                                        19
```